(12) United States Patent
Tsubota

(10) Patent No.: US 9,174,912 B2
(45) Date of Patent: Nov. 3, 2015

(54) POLYLACTIC ACID DECOMPOSITION METHOD

(75) Inventor: Jun Tsubota, Osaka (JP)

(73) Assignee: OSAKA GAS CO., LTD., Osaka-shi (JP)

( * ) Notice: Subject to any disclaimer, the term of this patent is extended or adjusted under 35 U.S.C. 154(b) by 0 days.

(21) Appl. No.: 13/807,802

(22) PCT Filed: Jun. 30, 2010

(86) PCT No.: PCT/JP2010/061182
§ 371 (c)(1),
(2), (4) Date: Dec. 31, 2012

(87) PCT Pub. No.: WO2012/001784
PCT Pub. Date: Jan. 5, 2012

(65) Prior Publication Data
US 2013/0095545 A1    Apr. 18, 2013

(51) Int. Cl.
| | |
|---|---|
| *C07C 55/00* | (2006.01) |
| *C07C 51/353* | (2006.01) |
| *C08J 11/28* | (2006.01) |
| *C08J 11/10* | (2006.01) |
| *C07C 51/09* | (2006.01) |

(52) U.S. Cl.
CPC .............. *C07C 51/353* (2013.01); *C07C 51/09* (2013.01); *C08J 11/105* (2013.01); *C08J 11/28* (2013.01); *C08J 2367/04* (2013.01); *Y02W 30/702* (2015.05); *Y02W 30/706* (2015.05)

(58) Field of Classification Search
CPC ...... C07C 51/09; C07C 51/353; C07C 59/08; C08J 11/28; C08J 11/105; C08J 2367/04
USPC ................. 435/167, 294.1; 562/589
See application file for complete search history.

(56) References Cited

U.S. PATENT DOCUMENTS

| | | | |
|---|---|---|---|
| 5,278,256 A * | 1/1994 | Bellis | 525/450 |
| 5,925,556 A | 7/1999 | Tokiwa et al. | |
| 2002/0123546 A1* | 9/2002 | Bigg et al. | 524/306 |

FOREIGN PATENT DOCUMENTS

| | | | |
|---|---|---|---|
| JP | 6-253865 A | | 9/1994 |
| JP | 9-111036 A | | 4/1997 |
| JP | 10-108670 A | | 4/1998 |
| JP | 2003 221461 | * | 8/2003 |
| JP | 2003-221461 A | | 8/2003 |
| JP | 221461 | * | 8/2003 |
| JP | 2005-095729 A | | 4/2005 |
| JP | 2005-206735 A | | 8/2005 |
| JP | 2005-232336 A | | 9/2005 |
| JP | 232336 | * | 9/2005 |
| JP | 2006-205017 A | | 8/2006 |
| JP | 2009-154125 | | 7/2009 |

OTHER PUBLICATIONS

JP 221461 (2003, as sited in the IDS filed Dec. 31, 2012) (An English translation conducted on a website named AIPN Japan Patent Office on Dec. 13, 2013).*
English machine translation of JP 221461, 2014.*
English machine translation of JP 232336, 2014.*
International Search Report for PCT/JP2010/061182, mailing date of Oct. 5, 2010.
Extended European Search Report dated Oct. 17, 2013, issued in corresponding European Patent Application No. 10854081.6.

* cited by examiner

*Primary Examiner* — Mark Shibuya
*Assistant Examiner* — Blaine G Doletski
(74) *Attorney, Agent, or Firm* — Westerman, Hattori, Daniels & Adrian, LLP

(57) ABSTRACT

A primary object of the present invention is to provide a polylactic acid decomposition method that efficiently decomposes polylactic acid so that the polylactic acid can readily undergo degradation by a biological treatment such as methane fermentation. Specifically, the present invention provides a polylactic acid decomposition method involving a step of impregnating a polylactic acid-containing organic material with a treatment solution containing an organic acid salt and/or inorganic acid salt of an amine compound.

7 Claims, 3 Drawing Sheets

POLYLACTIC ACID DECOMPOSITION METHOD

TECHNICAL FIELD

The present invention relates to a polylactic acid decomposition method that efficiently decomposes polylactic acid so that the polylactic acid can readily undergo degradation by a biological treatment, such as methane fermentation. The present invention further relates to a method for treating a polylactic acid-containing organic material using the decomposition method.

BACKGROUND ART

Because polylactic acid is biodegradable, many attempts have been made to develop applications of polylactic acid as a new-generation plastic. Products made from polylactic acid can be decomposed by microorganisms that are present in natural environments, in composts, etc. Therefore, polylactic acid products have an advantage in that they can be directly subjected to a biological treatment even when in admixture with easily degradable organic materials.

However, it has been found that while polylactic acid is prone to decompose in an aerobic atmosphere, polylactic acid is less susceptible to decomposition in an anaerobic atmosphere (see Patent Literature 1). Accordingly, if polylactic acid is subjected as is to methane fermentation, which requires an anaerobic atmosphere, the fermentation treatment has the disadvantage of taking a long time.

In view of the above, a method for solubilizing polylactic acid has been proposed wherein before subjecting the polylactic acid to methane fermentation, it is mixed with wastewater resulting from methane fermentation to thereby solubilize the polylactic acid at a temperature of about 50° C. to about 60° C. (see Patent Literature 2). However, when using this method, the final lactic acid yield is low, and polylactic acid cannot be efficiently solubilized; therefore, improved polylactic acid treatment efficiency and efficient energy recovery cannot be achieved by this method.

If lactic acid can be recovered after treating polylactic acid, recycling of resources can be achieved by providing a starting material for production of polylactic acid, which also contributes to global environmental protection and energy conservation. Accordingly, establishment of a technique for recovering lactic acid from polylactic acid has also been strongly desired by industry.

However, the above-mentioned polylactic acid solubilization method has the following problem. When using this method, polylactic acid is broken down into a lower molecular compound but partly remains as polymers or oligomers; therefore, lactic acid cannot be obtained with high recovery efficiency.

With such a background of prior art, there has been a desire for the development of a lactic acid production technique comprising efficiently decomposing polylactic acid, as well as an efficient energy recovery technique comprising subjecting polylactic acid to a decomposition treatment.

CITATION LIST

Patent Literature

PTL 1: Japanese Unexamined Patent Publication No. 2005-206735

PTL 2: Japanese Unexamined Patent Publication No. 2005-232336

SUMMARY OF INVENTION

Technical Problem

An object of the present invention is to provide a polylactic acid decomposition method that efficiently decomposes polylactic acid so that the polylactic acid can readily undergo degradation by a biological treatment, such as methane fermentation. Another object of the present invention is to provide a method for treating a polylactic acid-containing organic material using the polylactic acid decomposition method, and a system for treating a polylactic acid-containing organic material using the polylactic acid decomposition method.

Solution to Problem

To achieve the above objects, the present inventors conducted extensive research and found that when a polylactic acid-containing organic material is heated at a temperature of greater than 40° C. in the presence of an organic acid salt and/or inorganic acid salt of an amine compound represented by Formula (I) shown below, polylactic acid can be efficiently decomposed. The inventors conducted further research based on this finding and accomplished the present invention.

More specifically, the present invention provides a polylactic acid decomposition method and a system for treating a polylactic acid-containing organic material, as listed below.

Item 1. A method for treating a polylactic acid, comprising impregnating a polylactic acid-containing organic material with a treatment solution containing an organic acid salt and/or inorganic acid salt of an amine compound represented by Formula (I)

(wherein $R_1$, $R_2$, and $R_3$ are the same or different and represent hydrogen or $C_{1-5}$ alkyl) to perform a treatment.

Item 2. The method according to Item 1, wherein the organic acid salt and/or inorganic acid salt of an amine compound represented by Formula (I) has buffering capacity.

Item 3. The method according to Item 1, wherein the organic acid salt and/or inorganic acid salt of an amine compound represented by Formula (I) is at least one salt selected from the group consisting of ammonium carbonate, ammonium hydrogen carbonate, diammonium hydrogenphosphate, triammonium phosphate, ammonium borate, and triammonium citrate.

Item 4. The method according to Item 1, wherein the treatment is performed at a molecular ammonia concentration of 500 mg/L or more.

Item 5. The method according to Item 1, wherein the treatment is performed at a temperature of greater than 40° C.

Item 6. The method according to Item 1, wherein the treatment is performed at a pH of 8 to 9.

Item 7. The method according to Item 1, wherein the polylactic acid-containing organic material is a mixture of polylactic acid and garbage.

Item 8. A method for treating a polylactic acid-containing organic material comprising the steps of:
(a) impregnating the polylactic acid-containing organic material with a treatment solution containing an organic acid salt and/or inorganic acid salt of an amine compound represented by Formula (I)

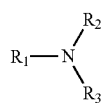

(wherein $R_1$, $R_2$, and $R_3$ are the same or different and represent hydrogen or $C_1$-$C_5$ alkyl) to decompose the polylactic acid; and
(b) subjecting the decomposition product obtained in step (a) to methane fermentation.

Item 9. The method according to Item 8, comprising heating the polylactic acid-containing organic material to a temperature of greater than 40° C. in the presence of molecular ammonia.

Item 10. The method according to Item 9, wherein the molecular ammonia has a concentration of 500 mg/L or more.

Item 11. The method according to Item 9, wherein the heating is performed at a pH of 8 to 9.

Item 12. A system for subjecting a polylactic acid obtained by decomposing a polylactic acid-containing organic material to methane fermentation, the system comprising
a polylactic acid decomposition tank for heating the polylactic acid-containing organic material and an organic acid salt and/or inorganic acid salt of an amine compound represented by Formula (I)

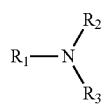

(wherein $R_1$, $R_2$, and $R_3$ are the same or different and represent hydrogen or $C_{1-5}$ alkyl)
to a temperature of greater than 40° C. to decompose the polylactic acid; and
a methane fermentation tank for subjecting the decomposed polylactic acid to methane fermentation,
wherein the decomposition tank comprises an ammonia stripping means and a means for returning the stripped ammonia to the decomposition tank to achieve a predetermined concentration.

Item 13. Use of an organic acid salt and/or inorganic acid salt of an amine compound represented by Formula (I)

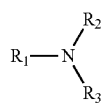

to decompose a polylactic acid.

Advantageous Effects of Invention

The decomposition method according to the present invention comprises heating a polylactic acid-containing organic material and an organic acid salt and/or inorganic acid salt of an amine compound represented by Formula (I) to a temperature of greater than 40° C. to remarkably improve polylactic acid decomposition efficiency. Thus, the decomposition method of the present invention can efficiently regenerate polylactic acid as lactic acid for use as a starting material, which can be resynthesized into polylactic acid after separation from solids other than polylactic acid. Alternatively, according to the method of the present invention, a polylactic acid can be converted to a substrate suitable for a biological treatment (particularly for methane fermentation treatment), thus reducing the total cost of polylactic acid decomposition using a biological treatment, and also reducing the amount of final residue after the biological treatment.

When the decomposition product obtained by the above decomposition method is further subjected to methane fermentation, conversion of the polylactic acid-containing organic material to final methane gas can proceed more efficiently, thus significantly increasing the amount of energy recovered as biogas.

Further, according to the system for treating a polylactic acid-containing organic material utilizing the aforementioned decomposition method, after decomposing a polylactic acid, ammonia stripping is preferably performed in a polylactic acid decomposition tank or other tank in order to inhibit adverse effects of ammonia in the subsequent methane fermentation process. At a pH of 7 or higher, ammonia can be easily recovered by ammonia stripping. Because lactic acid does not volatilize at all under the above-mentioned pH conditions, ammonia can be easily separated from an aqueous lactic acid solution and reused. The recovered lactic acid as is can be used as a starting material for synthesis of polylactic acid. Further, when the obtained decomposition product is to be converted to a fuel or when the purity of the obtained lactic acid is insufficient for synthesis of polylactic acid, the obtained product may be subjected to methane fermentation and recovered as methane, which can be utilized as energy.

DESCRIPTION OF EMBODIMENTS

The present invention is described in detail below.
1. Decomposition of Polylactic Acid
(1-1) Polylactic Acid
According to the decomposition method of the present invention, a polylactic acid-containing organic material is treated.

The polylactic acid contained in the organic material to be treated in the present invention is a polymer comprising lactic acid as a main constituent unit. In the present invention, the type of polylactic acid is not particularly limited, and examples thereof include lactic acid homopolymers such as poly-L-lactic acid and poly-D-lactic acid; lactic acid copolymers of at least one of L-lactic acid and D-lactic acid, and at least one member selected from the group consisting of alanine, glycolic acid, glycolide, glycine, s-caprolactone, glycol, polyethylene glycol, polypropylene glycol, polyvinyl alcohols, sugars, and polyhydric alcohols; poly-D,L,-lactic acid; and the like.

The organic material to be treated in the present invention may contain only one type of polylactic acid described above, or two or more types of such polylactic acids in combination.

A resin composition containing components other than polylactic acid may be used as the polylactic acid contained in the organic material to be treated. When a resin composition containing polylactic acid and one or more other components is used, the proportion of polylactic acid in the resin composition is not particularly limited and may be, for example, 5 to 99 wt %, preferably 20 to 99 wt %, and more preferably 50 to 99 wt %, based on the total weight of the resin composition. The resin composition may contain one or more additives for efficiently mixing polylactic acid and other resin compositions, or one or more additives for improving the physical properties of polylactic acid itself or a mixture of polylactic acid with other resin components. Although the proportion of such additives is not particularly limited, such additives are preferably used, for example, in an amount of not more than 10%, based on the total weight of the resin composition.

The polylactic acid to be treated in the present invention may be in any of various forms, such as a powder, a film, a non-woven fabric, a sheet, a plate, a foam, or an injection-molded product, and there is no particular limitation. When the polylactic acid is in the form of a film, a non-woven fabric, a sheet, a plate, a foam, an injection-molded product, or the like, the polylactic acid may be subjected to a pretreatment, such as pulverization or cutting, to form a powder or small pieces before performing the method of the present invention.

The organic material to be treated in the present invention may be polylactic acid alone or a mixture of polylactic acid with one or more other organic materials. Examples of the mixture of polylactic acid with one or more other organic materials include mixtures of polylactic acid with an organic material such as food waste, raw garbage, dried garbage, food factory waste, sewage sludge, and livestock waste (a mixture of livestock excrement with straw, sawdust, etc.). An organic material containing garbage and polylactic acid is particularly preferable as a material to be decomposed in the present invention. An advantage of the present invention is that the garbage collected in a garbage bag made from polylactic acid can be directly subjected to the decomposition method without separating the garbage from the garbage bag.

When a mixture of polylactic acid with one or more other organic materials is to be treated in the present invention, the polylactic acid and the organic materials are decomposed at the same time, thus reducing the total cost of treating all these materials.

(1-2) Organic Acid Salt and/or Inorganic Acid Salt of an Amine Compound Represented by Formula (I)

A feature of the polylactic acid decomposition method according to the present invention is impregnating a polylactic acid-containing organic material with a treatment solution containing an organic acid salt and/or inorganic acid salt of an amine compound represented by Formula (I) below. An amine compound represented by Formula (I) may be hereinafter simply referred to as an "amine compound". An organic acid salt and/or inorganic acid salt of the amine compound may be simply referred to as a "salt of the amine compound".

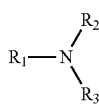
(I)

(In Formula (I), $R_1$, $R_2$, and $R_3$ may be the same or different and represent hydrogen or $C_{1-5}$ alkyl.)

In Formula (I), $R_1$, $R_2$, and $R_3$ are the same or different and represent hydrogen or $C_{1-5}$ alkyl. Examples of $C_{1-5}$ alkyl include methyl, ethyl, propyl, isopropyl, butyl, isobutyl, sec-butyl, tert-butyl, pentyl, isopentyl, and neopentyl. From the viewpoint of increased efficiency of decomposition of polylactic acid into lactic acid, it is preferable that $R_1$, $R_2$, and $R_3$ are the same or different and represent hydrogen, methyl, ethyl, propyl, or isopropyl; it is more preferable that $R_1$, $R_2$, and $R_3$ are the same or different and represent hydrogen, methyl, or ethyl; it is even more preferable that $R_1$ and $R_2$ are hydrogen, and $R_3$ is hydrogen, methyl, or ethyl; it is particularly preferable that $R_1$ and $R_2$ are hydrogen and $R_3$ is hydrogen, methyl, or ethyl; and it is more particularly preferable that $R_1$, $R_2$, and $R_3$ are hydrogen.

In the organic acid salt and/or inorganic acid salt of an amine compound represented by Formula (I), the amine compound of Formula (I) is in the form of a cation represented by Formula (II) below, which forms a salt with an organic or inorganic acid. In Formula (II), $R_1$, $R_2$, and $R_3$ are as defined in Formula (I) above.

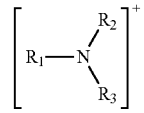
(II)

Examples of the salt of the amine compound include salts with inorganic acids, such as carbonic acid, phosphoric acid, phosphorous acid, boric acid, nitric acid, sulfuric acid, and oxalic acid; and salts with organic acids, such as formic acid, lactic acid, and citric acid. Hydrogen salts or metal salts thereof may also be used. Specific examples thereof include inorganic acid salts such as ammonium carbonate, ammonium hydrogen carbonate, diammonium hydrogenphosphate, triammonium phosphate, ammonium borate, ammonium nitrate, ammonium dihydrogen phosphite, ammonium dihydrogen phosphate, ammonium hydrogen sulfate, ammonium oxalate, ammonium iron(II) sulfate, ammonium iron(III) sulfate, and ammonium peroxodisulfate; and organic acid salts such as ammonium formate, diammonium hydrogen citrate, triammonium citrate, and ammonium lactate. Such salts may be used singly or in a combination of two or more.

The salt of the amine compound used in the present invention preferably has pH buffering capacity (which may be simply referred to as having "buffering capacity" in this specification). The salt of the amine compound having buffering capacity is preferably a salt with carbonic acid, phosphoric acid, or boric acid. Specific examples thereof include ammonium carbonate, ammonium hydrogen carbonate, triammonium phosphate, and ammonium borate.

The treatment solution containing an organic acid salt and/or inorganic acid salt of the amine compound may be in the form of an aqueous ammonia solution formed by dissolution of a salt of the amine compound in water or the like and salt elimination. However, when the salt of an amine compound does not have buffering capacity or when aqueous ammonia is used, the solution is preferably adjusted to a suitable pH environment before performing the method of the present invention, as described below.

In the decomposition method of the present invention, the concentration of the salt of the amine compound during the treatment is not particularly limited insofar as polylactic acid can be decomposed. The salt concentration is 0.1 wt % or more, typically 0.1 to 10 wt %, preferably 0.1 to 5 wt %, and more preferably 1 to 5 wt %, based on the total weight of the polylactic acid-containing organic material to be treated.

The salt of the amine compound used in the present invention is present as ammonia molecules in the treatment solution. This is considered to contribute to the decomposition of polylactic acid. Accordingly, it is preferable in the present invention that the temperature, pH, and concentration of the amine compound be adjusted in such a manner that molecular ammonia is present in the treatment solution in an amount sufficient for the decomposition of polylactic acid.

The concentration of the molecular ammonia in the treatment solution can be determined based on the concentration of the amine compound salt and is not particularly limited. The concentration may be, for example, 500 mg/L or more, preferably 1,000 to 100,000 mg/L or more, and more preferably 1,000 to 10,000 mg/L or more.

The concentration of the molecular ammonia is affected by the pH environment and temperature conditions, as shown in the following Formulas A and B:

$$[NH_3] = \frac{Ka}{[H^+]} \cdot [NH_4^+] \quad \text{Formula (A)}$$

$$\log Ka = 0.09018 + 2730/(T + 273) \quad \text{Formula (B)}$$

wherein Ka represents a dissociation equilibrium constant of ammonium ion, and T represents a temperature (° C.).

Accordingly, in the decomposition method of the present invention, the pH environment and temperature conditions are appropriately adjusted, based on Formulas (A) and (B), within the pH and temperature numerical ranges described below to adjust the molecular ammonia concentration to the above-mentioned range.

The pH environment in the decomposition method of the present invention is not particularly limited insofar as it does not hinder the decomposition of polylactic acid. The pH is about 7 to about 11, preferably about 7.5 to about 9.5, and more preferably about 8 to about 9. To create such a pH environment, an alkali conventionally used for pH adjustment, such as sodium hydroxide, can be used.

Methane fermentation sludge contains a salt of the amine compound, typically contains molecular ammonia in a concentration of 100 to 3,000 mg/L, and is known to have buffering capacity. Accordingly, methane fermentation sludge can be used as a treatment solution containing a salt of the amine compound in the method of the present invention. The methane fermentation sludge as used herein refers to a sludge component obtained by subjecting an organic material to methane fermentation. The methane fermentation refers to fermentation performed in the presence of both an organic material and methane fermentation bacteria in an anaerobic atmosphere, and methane is produced as a final metabolite. In the preparation of methane fermentation sludge, there is no particular limitation on the type of methane fermentation bacteria, the type of organic material used as a substrate, etc. When the decomposition product obtained by the decomposition method of the present invention is further subjected to methane fermentation and continuously treated, it is preferable from the viewpoint of system efficiency that sludge produced by methane fermentation be used for the decomposition of polylactic acid.

The methane fermentation sludge used in the present invention may be a fermented product itself that is obtained by subjecting an organic material to methane fermentation treatment, or it may be the solids or liquid separated from the fermented product. Alternatively, a fermented product from which relatively large solids have been removed by using a screw press filter or the like may be used as methane fermentation sludge in the present invention. Preferably, the methane fermentation sludge is a fermented product itself obtained by subjecting an organic material to methane fermentation.

In the decomposition method of the present invention, the proportion of the methane fermentation sludge added to the polylactic acid-containing organic material can be appropriately set according to the types of methane fermentation sludge and polylactic acid used, and other conditions, based on the amount of molecular ammonia added. For example, the methane fermentation sludge is used in a proportion of 0.01 to 10 parts by weight (based on solids), and preferably 0.1 to 1 part by weight, per part by weight of polylactic acid (based on the weight of polylactic acid when using a resin composition containing components other than polylactic acid).

As described above, when using a salt of the amine compound, polylactic acid can be decomposed into lactic acid. Accordingly, a mode of use of an organic acid salt and/or inorganic acid salt of the amine compound to decompose polylactic acid is provided.

(1-3) Reaction Conditions

Because ammonia is not consumed in the decomposition method of the present invention, polylactic acid can be continuously fed and treated. There is no particular limitation on the amount of polylactic acid in the reaction tank; for example, an organic material, containing polylactic acid in an amount of 0.1 to 1,000 kg, preferably 10 to 100 kg, per m$^3$ of the treatment solution, is impregnated into the amine compound salt-containing treatment solution and incubated.

The term "impregnating" as used herein refers to any treatment that can bring a polylactic acid-containing organic material into contact with the treatment solution. For example, "impregnating" includes immersion of the organic material in the treatment solution, stirring, etc. Alternatively, the treatment solution may be sprayed over the surface of a polylactic acid-containing organic material to bring the solution and the organic material into contact with each other. The "treatment" refers to causing a polylactic acid-containing organic material and the treatment solution to coexist, and may include heating, as desired.

The decomposition treatment time in the present invention may vary depending on the type and amount of methane fermentation sludge used and the type and amount of polylactic acid to be treated, and it cannot be specified uniformly. However, the decomposition treatment is typically performed for 1 to 192 hours, preferably 10 to 96 hours, and more preferably 24 to 48 hours.

In the decomposition method of the present invention, as long as the concentration of molecular ammonia can be adjusted to the above-mentioned concentration range, the temperature conditions are not particularly limited and can be appropriately set using Formulas (A) and (B) shown above. For example, the temperature may be 40° C. or more, preferably about 40° C. to about 100° C., more preferably over 40° C. to about 100° C., still preferably 50 to 100° C., even more preferably about 65.5° C. to about 100° C., still even more preferably about 68° C. to about 90° C., and particularly preferably about 75° C. to about 85° C. When methane fermentation sludge is used in the decomposition method of the present invention, the temperature is preferably 65.5° C. or more.

When the temperature is within the above-mentioned range, polylactic acid can be efficiently composed. However, when the reaction solution does not have a sufficiently high ammonia concentration, for example, when methane fermentation sludge is used, polylactic acid may not be sufficiently decomposed at a temperature of lower than 70° C. due to a low molecular ammonia concentration. To maintain a predetermined temperature of 65.5° C. or more in the decomposition method of the present invention, fuel oil, city gas, electric power, or the like may be used. When organic waste decomposed by the method of the present invention is further subjected to methane fermentation, it is preferable to use a cogeneration means (e.g., a gas engine or fuel cell) that generates heat and electric power by utilizing methane gas produced by methane fermentation, rather than fuel oil or the like, in order to maintain the temperature during the sludge treatment, and the generated heat is preferably used for heating in the sludge treatment.

The decomposition method of the present invention is performed by causing polylactic acid and a salt of the amine compound (or molecular ammonia or methane fermentation sludge) to coexist, and leaving these as is or stirring under the above-mentioned temperature conditions.

Because molecular ammonia is prone to volatilize upon heating and is difficult to maintain at a predetermined concentration, the decomposition method of the present invention is preferably performed in a closed atmosphere to prevent the release of ammonia outside the system.

When methane fermentation sludge is used in the decomposition method of the present invention, the decomposition treatment is performed in an anaerobic atmosphere. The method of creating an anaerobic atmosphere is not particularly limited and includes, for example, purging the decomposition tank with an inert gas, such as nitrogen gas.

The decomposition treatment in the present invention may be performed in batch, or it may be performed in continuous mode in which feeding of polylactic acid and methane fermentation sludge and removal of a polylactic acid decomposition product obtained using methane fermentation sludge are performed continuously or intermittently. When the feeding and removal are continuously or intermittently performed, the feeding rate and removal rate can be appropriately set so that the average residence time will be the aforementioned treatment time.

The decomposition method of the present invention can be performed in a tank capable of adjusting and maintaining the aforementioned treatment conditions (hereinafter referred to as "sludge treatment tank"). Specific methods for feeding polylactic acid and methane fermentation sludge to the sludge treatment tank include the following:

(i) a method comprising separately feeding polylactic acid and methane fermentation sludge to a sludge treatment tank and mixing the polylactic acid and the methane fermentation sludge in the tank; and
(ii) a method comprising feeding polylactic acid and methane fermentation sludge to a mixing tank equipped with a mixing means to premix the polylactic acid and the methane fermentation sludge, and feeding the mixture to a sludge treatment tank.

Thus, polylactic acid can be efficiently decomposed. When polylactic acid is decomposed using aqueous ammonia in a conventional manner, an amide compound of lactic acid is produced. However, when polylactic acid is decomposed using a salt of the amine compound, the decomposition product does not include such an amide compound, oligomers, etc., and nearly 100% lactic acid is obtained. Accordingly, the thus obtained polylactic acid decomposition product (lactic acid) can be preferably reused as a starting material for production of polylactic acid. In contrast, when methane fermentation sludge is used, the obtained polylactic acid decomposition product contains impurities; therefore, the decomposition product is preferably used as a substrate of methane fermentation. The polylactic acid decomposition product obtained by the decomposition method of the present invention (hereinafter sometimes simply referred to as "decomposition product") is a lower molecular compound broken down from polylactic acid, and thus can be easily used as a substrate by microorganisms, such as methane fermentation bacteria. Therefore, by further subjecting the decomposition product obtained by the decomposition method of the present invention to a biological treatment, such as methane fermentation treatment or activated sludge treatment, the polylactic acid decomposition rate in the biological treatment can be increased.

2. Methane Fermentation Treatment

When the decomposition product obtained by the decomposition method of the present invention contains impurities such as lactic acid oligomers, the decomposition product may be further subjected to a biological treatment method. As a specific example of such a method, a methane fermentation method is described below to explain a method for treating a polylactic acid-containing organic material.

The decomposition product obtained by the above decomposition method may be directly subjected to methane fermentation. Alternatively, after subjecting the decomposition product to solid-liquid separation, the liquid may be subjected to methane fermentation.

When the decomposition product obtained by the above decomposition method is subjected to solid-liquid separation, the solid-liquid separation method is not particularly limited, and any known method can be used. For example, when the solids in the decomposition product are susceptible to sedimentation, the solid-liquid separation can be performed by precipitation separation. Other examples of usable methods include membrane separation, centrifugation, and the like. The solid-liquid separation may be performed for all of the decomposition product obtained by the above decomposition method. Alternatively, part of the decomposition product may be subjected to solid-liquid separation, and the rest may be directly subjected to methane fermentation described below. In this case, it is unnecessary to stop the whole system when maintenance of the solid-liquid separation means is performed.

When the decomposition product obtained by the above decomposition method is subjected to solid-liquid separation, all or part of the obtained solids-containing fraction (sludge) may be treated again by the above decomposition method, or part thereof may be disposed of.

The decomposition product obtained by the decomposition method may be directly subjected to methane fermentation in an anaerobic atmosphere, or the solids separated from the decomposition product may be subjected to the methane fermentation. In the methane fermentation treatment, the decomposition product obtained by the decomposition method of the present invention is separated into methane and carbon dioxide, and the methane fermentation can be performed using known methane fermentation bacteria and a methane fermentation tank.

The methane fermentation temperature conditions in the methane fermentation treatment can be appropriately selected from a wide temperature range according to the type of methane fermentation bacteria used, and there is no particular limitation on the temperature conditions. The temperature is typically about 20° C. to about 60° C., and may be, for example, a "medium" temperature of about 35° C., or a "high" temperature of about 55° C. When the decomposition product obtained by the above decomposition method has low nitrogen content and when ammonia removal is not performed in the treatment according to the decomposition method, a medium temperature of about 35° C. is preferable because methane fermentation is less susceptible to ammonia inhibition at such a temperature. In contrast, when ammonia removal is performed in the treatment according to the decomposition method, a high temperature of about 55° C. is preferable in view of increasing the methane fermentation rate.

When the decomposition product obtained by the above decomposition method maintains a high temperature of about 80° C. or more, the decomposition product is preferably cooled down to a temperature that does not significantly adversely affect methane fermentation (for example, about 60° C. or less) before subjecting the decomposition product to methane fermentation treatment.

The methane fermentation treatment time in the methane fermentation treatment may vary according to the types and amounts of decomposition product and fermentation bacteria used, fermentation temperature, fermentation form, etc., and cannot be specified uniformly. However, the methane fermentation treatment is typically performed for 14 to 30 days, preferably 10 to 20 days, and even more preferably 10 to 14 days.

According to the conventional method comprising directly subjecting polylactic acid and organic waste to methane fermentation, the sludge generated by methane fermentation (waste sludge) is disposed of. However, in the present invention, the waste sludge can be periodically returned to sludge treatment in the above decomposition method and used, so that the sludge can be decomposed again by the decomposition treatment, thus increasing the final polylactic acid decomposition rate.

In the methane fermentation treatment, the format of methane fermentation is not particularly limited. Any known format that is used in methane fermentation, such as a batch system, a fixed bed system, an UASB (Upflow Anaerobic Sludge Bed) system, may be used. The feeding of the decomposition product obtained by the above decomposition method and removal of the methane fermentation product from the methane fermentation tank may be performed continuously or intermittently. When the feeding of the decomposition product and removal of the methane fermentation product are performed continuously or intermittently, the decomposition product feeding rate and the methane fermentation product removal rate can be appropriately set so that the average residence time of the decomposition product in the methane fermentation tank will be the above-mentioned fermentation treatment time.

The methane fermentation product obtained by the methane fermentation treatment may be directly subjected to water treatment such as activated sludge treatment, or the liquid after solid-liquid separation may be subjected to water treatment. The solid-liquid separation method is not particularly limited, and examples of usable methods include known methods such as precipitation separation, membrane separation, and centrifugation. All or part of the methane fermentation product may be subjected to solid-liquid separation.

A part or all of the solids-containing fraction (sludge) obtained by solid-liquid separation of the methane fermentation product may be returned to the methane fermentation tank and subjected to methane fermentation treatment. This operation can more thoroughly decompose the solids and thus further reduce the amount of waste solids and increase the methane gas yield. In addition to these advantages, the stability of methane fermentation is also enhanced because methanogen is returned to the system. However, an increased return ratio increases the solids content in the methane fermentation tank, which is disadvantageous for stirring in the methane fermentation tank and for pumping. Accordingly, the amount of return should be determined based on comprehensive consideration of all these factors.

In the methane fermentation treatment, the solids are accumulated in the methane fermentation tank as the fermentation progresses. Therefore, the solids are usually removed as sludge from the tank during the fermentation, as required. The removed sludge can be treated by various methods. For example, the sludge as is may be applied to farmland as a liquid fertilizer, or it may be composted after dewatering and then applied to farmland. Alternatively, the sludge may be subjected to a treatment, such as disposal after dewatering, disposal after dewatering and drying, incineration after dewatering, disposal after dewatering and drying, or incineration after dewatering and drying. In such a treatment, to eliminate user aversion, it is important that no polylactic acid remains. Furthermore, low-temperature waste heat can be effectively used for drying. When methane gas is used for a gas engine, a micro gas turbine, a boiler, or the like, the waste heat can be utilized for drying.

The filtrate from dewatering may be directly released depending on its water quality and effluent standard. When the filtrate cannot be released as is, it may be subjected to water treatment again. The methane fermentation treatment is performed in an anaerobic atmosphere. Therefore, when the water treatment is a treatment performed in an aerobic atmosphere, such as activated sludge treatment, the polylactic acid not decomposed by methane fermentation or a decomposition product thereof may be decomposed by water treatment, such as activated sludge treatment. This reduces the amount of sludge to be disposed of and is thus preferable.

3. Polylactic Acid Decomposition System

The present invention further provides a polylactic acid decomposition system utilizing the above polylactic acid decomposition method. Specifically, the present invention provides a decomposition system comprising a polylactic acid decomposition tank for heating a polylactic acid-containing organic material and a salt of the amine compound to a temperature of 40° C. or more to decompose a polylactic acid, and a methane fermentation tank for subjecting the polylactic acid decomposition product to methane fermentation, wherein the decomposition chamber comprises an ammonia stripping means, and a means for returning the stripped ammonia to the decomposition tank to achieve a predetermined concentration.

The polylactic acid decomposition system according to the present invention comprises a polylactic acid decomposition tank and a methane fermentation tank. A feature of the polylactic acid decomposition tank used herein is that the tank comprises a heating means that can heat a polylactic acid-containing organic material and a salt of the amine compound (or molecular ammonia) to a temperature higher than 40° C., an ammonia stripping means, and a means for returning stripped ammonia to the decomposition tank. Another feature of the decomposition system according to the present invention is that the system comprises a methane fermentation tank in which the polylactic acid decomposed in the decomposition tank is subjected to methane fermentation.

The ammonia stripping means and the ammonia feeding means are used for removal and feeding of ammonia to adjust the concentration of ammonia in the decomposition tank to a predetermined concentration as described above. The ammonia removed by the ammonia stripping means is collected and can be fed when the concentration of molecule ammonia is not sufficient in the next decomposition treatment.

The methane fermentation chamber is not particularly limited insofar as feeding of the polylactic acid decomposition product and removal of the methane fermentation product from the methane fermentation tank can be continuously or intermittently performed. Conventional means can be used.

EXAMPLES

The present invention is described below with reference to Test Examples. However, the scope of the invention is not limited to these Test Examples. In all Test Examples, the same polylactic acid was used.

Test Example 1

Ammonium carbonate (produced by Kishida Chemical Co., Ltd., was added to water containing an excessive amount of polylactic acid (Poly-L-lactide: produced by NatureWorks LLC; polylactic acid concentration=1 g/20 ml) in such amounts that the resulting mixtures contained molecular ammonia at different concentrations ranging from 500 to 50,000 mg/L.

The higher the production rate of lactic acid was, the higher was the concentration of molecular ammonia in a solution. For example, at an ammonium carbonate concentration of 25 wt %, at a temperature of 95° C. and at a pH of 8.8, the concentration of molecular ammonia was 50,423 mg/L, and the lactic acid production rate in this case was 854.7 µg/sec-L (see FIG. 1).

The lactic acid production rate was calculated according to the following formula.

Lactic acid production rate=weight of produced lactic acid/(reaction time×amount of reaction mixture) [Equation 3]

Furthermore, in this test, NMR measurement revealed that the produced lactic acid did not contain lactic acid amide. Analysis of the amounts of lactic acid and lactic acid amide was conducted using a T-NMR (ECX-400) (400 MHz) manufactured by JEOL Ltd. under the following conditions: solvent: THF-d8; measurement nucleus: 1H; measurement temperature: room temperature (about 25° C.); and chemical shift standard: room temperature (about 25° C.) FIG. 2 shows the results. As shown in FIG. 2, the soluble matter was all collected as a lactic acid monomer, and lactic acid amide was not present (see FIG. 2).

The results show that the polylactic acid decomposition method of the present invention has several advantages over Comparative Example 1, which will be described below; i.e., the lactic acid production rate is significantly faster, ammonia is not consumed, and the collected lactic acid is not amidated.

Test Example 2

Ammonium carbonate (manufactured by Kish da Chemical Co., Ltd.) was added to water (polylactic acid concentration=1 g/20 ml) containing an excessive amount of polylactic acid to make mixtures with different concentrations ranging from 500 to 50,000 mg/L. FIG. 3 shows the lactic acid production rate at reaction temperatures of 40° C. and 45° C. The lactic acid production rate was calculated according to the above formula.

As shown in FIG. 3, lactic acid was not produced at 40° C. However, at a reaction temperature of 45° C., when the concentration of molecular ammonia exceeded 7,000 mg/L, lactic acid was produced.

Test Example 3

Each ammonium salt shown in the table below was individually added to a separate 2-ml amount of water containing 0.02 g of polylactic acid to make the concentration of ammoniacal nitrogen equal to 10,000 mg/L. The lactic acid production rate at a reaction temperature of 70° C. is also shown in the table below. The lactic acid production rate was calculated according to the above formula.

TABLE 1

| Added Ammonium Salt | pH | Lactic Acid Production Rate (µg/sec-L) |
|---|---|---|
| Ammonium Formate | 6.4 | 0.8 |
| Ammonium Nitrate | 5.9 | 5.5 |
| Ammonium Dihydrogen Phosphite | 4.0 | 3.1 |
| Ammonium Lactate Solution (50%) | 4.7 | 8.4 |
| Ammonium Dihydrogen Phosphate | 4.6 | 1.5 |
| Ammonium Hydrogen Sulfate | 1.5 | 4.2 |
| Diammonium Hydrogen Phosphate | 8.1 | 58.9 |
| Ammonium Oxalate | 6.8 | 8.9 |
| Triammonium Phosphate | 9.4 | 174.0 |
| Diammonium Hydrogen Citrate | 5.2 | 5.6 |
| Ammonium Peroxodisulfate | 4.5 | 9.7 |
| Triammonium Citrate | 7.4 | 19.5 |
| Ammonium Iron (II) Sulfate | 4.3 | 2.5 |
| Ammonium Iron (III) Sulfate | 2.4 | 7.1 |
| Ammonium Borate | 8.3 | 238.6 |
| Ammonium Hydrogen Carbonate | 8.1 | 133.3 |
| Ammonium Carbonate | 9.1 | 199.0 |

According to the results, not only ammonium carbonate but also an ammonium salt with pH buffering capacity such as ammonium borate brings about the advantageous effect of the present invention, when added.

According to the results, the decomposition rate was low with compounds having a pH of 7 or below after dissolution. However, it is expected that such an advantageous effect achieved with other salts is obtained when a suitable alkali, such as sodium hydroxide, is added to adjust the pH to 7 or above.

Moreover, it is also expected that the same effect as achieved with the above-mentioned ammonium salts is obtained when ammonia derivatives (e.g., methylammonium and ethylammonium) are used.

Test Example 4

One gram of a garbage bag (40 µm in thickness) containing, as basic components, 70% polylactic acid (Poly-L-lactide: produced by NatureWorks LLC) and 30% polybutylene adipate terephthalate (manufactured by BASF) was put into 20 ml of methane fermentation sludge (ammoniacal nitrogen concentration=2,500 mg/L, pH of 8, and 0.4 part by weight of methane fermentation sludge (calculated as solid) relative to 1 part by weight of polylactic acid), and the reaction temperature was set to 80° C. In this case, the lactic acid production rate was 216.7 µg/sec-L. The lactic acid production rate in this case was calculated according to the above formula.

Comparative-Example 1

Alkali Decomposition of Polylactic Acid Using Ammonia Water

Comparative Example

Alkali Hydrolysis

First, 10 g of polylactic acid was added to 10 ml of water, and the pH was adjusted to 8.5, 9.5, or 10.5 as a default value using 25 vol % of ammonia water to initiate decomposition at 70° C. Since lactic acid was produced as the polylactic acid was decomposed, and the pH of the reaction mixture was lowered, 25 vol % of ammonia water was added as necessary so that the pH was maintained at the default value. During the process of decomposition, the concentration of the produced lactic acid was measured over time.

Table 2 shows the cumulative amount of ammonia added to the reaction liquid in each case until the concentration of lactic acid reached 0, 1, 5, and 10 g/l in each condition.

In each condition, when the concentration of lactic acid in the reaction liquid increased from 0 g/l to 5 g/l, the ratio of the increase in the cumulative amount of added ammonia to the increase in the concentration of lactate acid was substantially constant. In other words, when the concentration of lactic acid increased from 0 g/l to 5 g/l, a proportional relationship was observed between the cumulative amount of the added ammonia and the concentration of lactic acid. This is considered to be because ammonia was used for resisting a decrease in pH caused by the produced lactic acid.

On the other hand, in each condition, when the concentration of lactic acid in the reaction liquid increased from 5 g/l to 10 g/l, the ratio of the increase in the cumulative amount of added ammonia to the increase in the concentration of lactic acid obviously rose. This shows that when the concentration of lactic acid increased from 5 g/l to 10 g/l, the produced lactic acid was amidated, and ammonia was used as a substrate for forming the amidated product.

TABLE 2

| | Concentration of Lactic Acid in Reaction Liquid | | | |
|---|---|---|---|---|
| | 0 g/l | 1 g/l | 5 g/l | 10 g/l |
| Cumulative Amount of Added Ammonia (pH default value of 8.5) | 0.01 mg | 1.9 mg | 9.46 mg | 28.9 mg |
| Cumulative Amount of Added Ammonia (pH default value of 9.5) | 0.03 mg | 1.92 mg | 9.47 mg | 28.9 mg |
| Cumulative Amount of Added Ammonia (pH default value of 10.5) | 0.8 mg | 2.69 mg | 10.25 mg | 29.7 mg |

The lactic acid production rates in the above conditions were 1.2 μg/sec-L (at a pH default value of 8.5), 15 μg/sec-L (at a pH default value of 9.5), and 109 μg/sec-L (at a pH default value of 10.5), and all were significantly lower than in Test Example 1 above. The lactic acid production rate was calculated according to the above formula.

Figure 1:
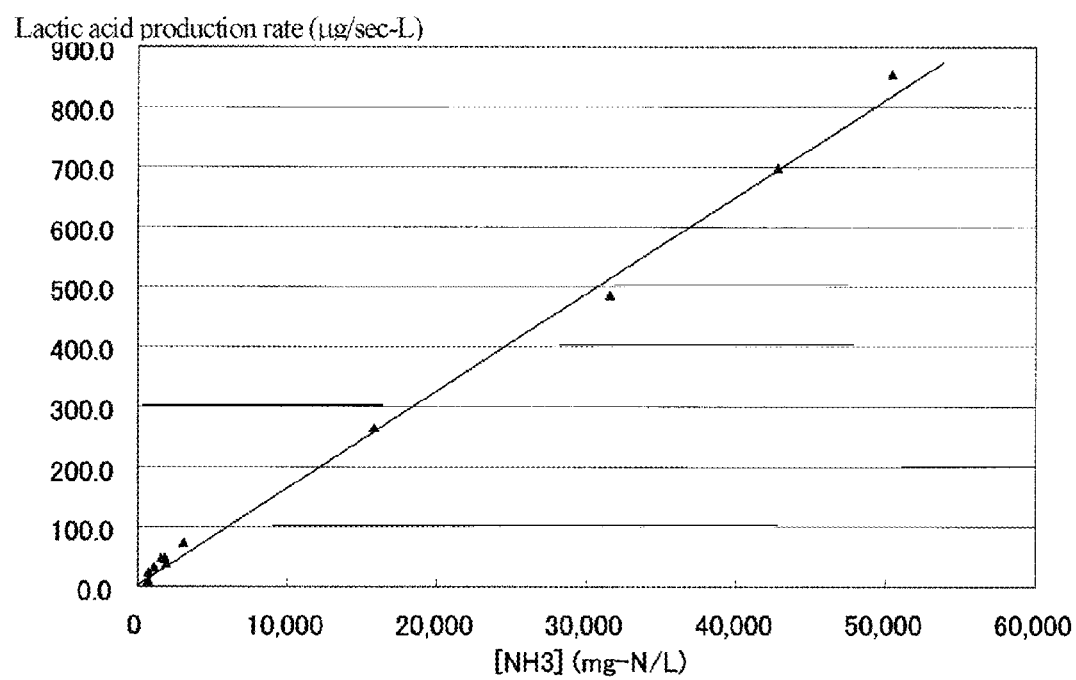
FIG. 1 is a graph showing the lactic acid production rate in Test Example 1.
Figure 2:
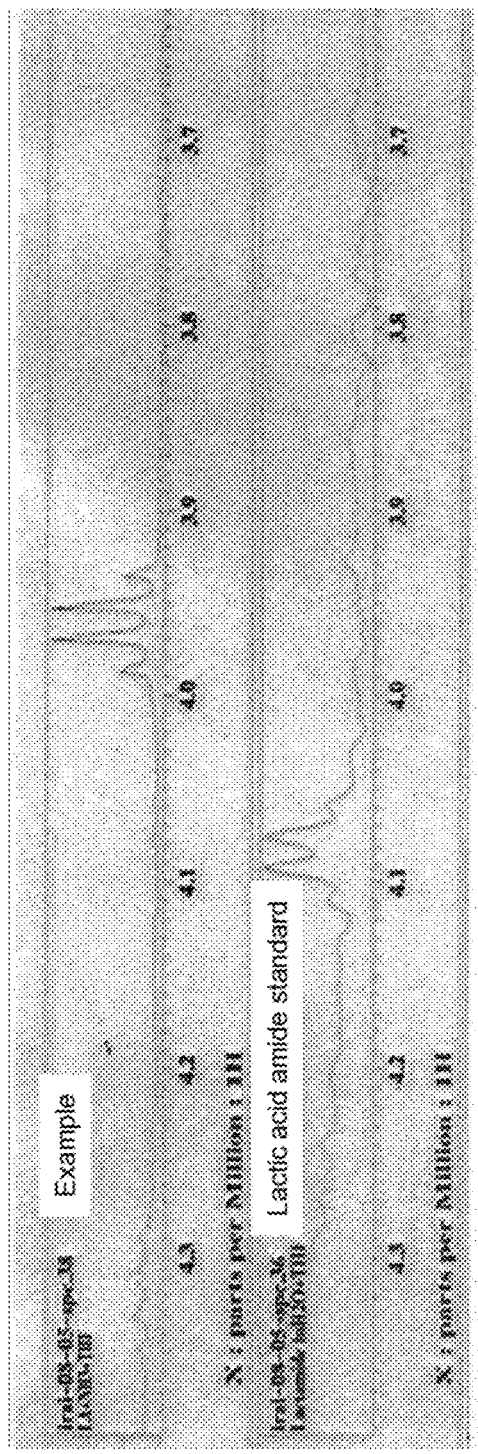
FIG. 2 is a graph showing that lactic acid obtained in Test Example 1 was not amidated.
Figure 3:
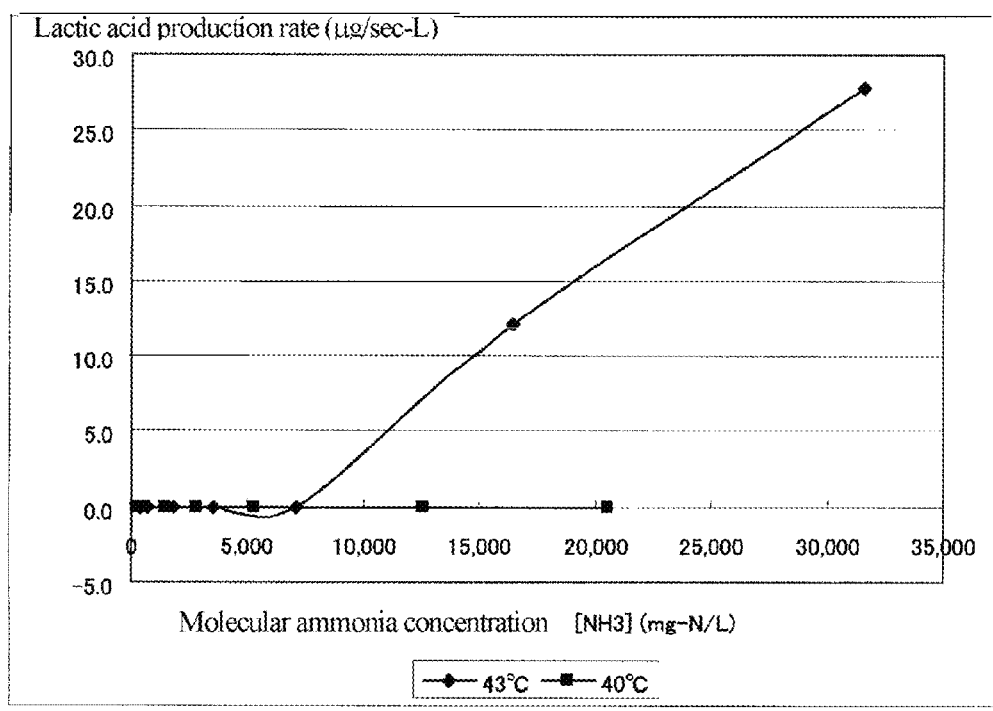
FIG. 3 is a graph showing the lactic acid production rate in Test Example 2.

The invention claimed is:

1. A method for treating a polylactic acid, comprising impregnating a polylactic acid-containing organic material with a treatment solution containing a salt consisting of anion of an organic acid and/or inorganic acid, and cation of an amine compound, wherein the cation is represented by Formula (II)

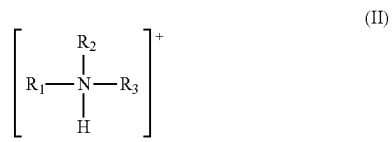

wherein $R_1$, $R_2$, and $R_3$ are the same or different and represent hydrogen or $C_{1-5}$ alkyl to perform a treatment, wherein the treatment is performed at a temperature of greater than 40° C., wherein the salt has buffering capacity and wherein the salt is at least one salt selected from the group consisting of ammonium hydrogen carbonate, diammonium hydrogenphosphate, triammonium phosphate, ammonium borate, and triammonium citrate.

2. The method according to claim 1, wherein the treatment is performed at a molecular ammonia concentration of 500 mg/L or more.

3. The method according to claim 1, wherein the treatment is performed at a pH of 8 to 9.

4. The method according to claim 1, wherein the polylactic acid-containing organic material is a mixture of polylactic acid and garbage.

5. A method for treating a polylactic acid-containing organic material comprising the steps of:

(a) impregnating the polylactic acid-containing organic material with a treatment solution containing a salt consisting of anion of an organic acid and/or inorganic acid, and cation of an amine compound, wherein the cation is represented by Formula (II)

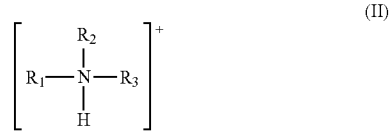

wherein $R_1$, $R_2$, and $R_3$ are the same or different and represent hydrogen or $C_{1-5}$ alkyl to decompose the polylactic acid; and (b) subjecting the decomposition product obtained in step (a) to methane fermentation, wherein the treatment in step (a) is performed at a temperature of greater than 40° C., wherein the salt has buffering capacity and wherein the salt is at least one salt selected from the group consisting of ammonium hydrogen carbonate, diammonium hydrogenphosphate, triammonium phosphate, ammonium borate, and triammonium citrate.

6. The method according to claim 5, wherein the treatment in step (a) is performed at a molecular ammonia concentration of 500 mg/L or more.

7. The method according to claim 5, wherein the treatment in step (a) is performed at a pH of 8 to 9.

* * * * *